(12) United States Patent
Petersen et al.

(10) Patent No.: US 6,657,718 B1
(45) Date of Patent: Dec. 2, 2003

(54) MEASURING CELL FOR LIQUIDS

(75) Inventors: Karl Petersen, Norderstedt (DE); Ludger Middelberg, Kaltenkirchen (DE)

(73) Assignee: Bran + Luebbe GmbH, Norderstedt (DE)

( * ) Notice: Subject to any disclaimer, the term of this patent is extended or adjusted under 35 U.S.C. 154(b) by 0 days.

(21) Appl. No.: 09/622,742

(22) PCT Filed: Feb. 16, 1999

(86) PCT No.: PCT/EP99/00999

§ 371 (c)(1),
(2), (4) Date: Aug. 22, 2000

(87) PCT Pub. No.: WO99/44038

PCT Pub. Date: Sep. 2, 1999

(30) Foreign Application Priority Data

Feb. 27, 1998 (DE) .......................................... 198 08 164

(51) Int. Cl.⁷ ............................. G01N 1/10; G01N 21/05
(52) U.S. Cl. ...................... 356/246; 356/338; 356/410; 356/411; 250/573
(58) Field of Search ................................. 356/409, 410, 356/440, 442, 246, 236, 441, 338; 250/575, 576, 432 R, 573

(56) References Cited

U.S. PATENT DOCUMENTS

| 3,920,332 A | 11/1975 | Steichen et al. |
| 3,998,592 A | 12/1976 | Pyle |
| 4,236,076 A | 11/1980 | Judge et al. |
| 4,278,887 A | * 7/1981 | Lipshutz et al. ........ 250/432 R |
| 4,566,791 A | * 1/1986 | Goldsmith ................... 250/573 |
| 4,566,891 A | 1/1986 | Briar et al. |
| 4,580,901 A | 4/1986 | Goldsmith |
| 5,046,854 A | 9/1991 | Weller et al. |
| 5,386,121 A | * 1/1995 | Barbee et al. ........... 250/341.8 |
| 5,636,017 A | * 6/1997 | Bruno et al. ................. 356/246 |
| 5,726,752 A | * 3/1998 | Uno et al. ................... 356/246 |

FOREIGN PATENT DOCUMENTS

| DE | 1 761 394 | 2/1958 |
| DE | 19 20 214 | 7/1965 |
| DE | 1 673 108 | 5/1970 |
| DE | 73 33 009.3 | 3/1974 |
| DE | 31 03 476 A1 | 12/1981 |
| DE | 89 13 786.8 | 3/1990 |
| WO | 80/00188 | 2/1980 |

* cited by examiner

Primary Examiner—Richard A. Rosenberger
Assistant Examiner—Vincent P. Barth
(74) Attorney, Agent, or Firm—Baker & Hostetler LLP

(57) ABSTRACT

A liquid measuring cell for measuring optical properties of liquids, with a measuring chamber (16), which is adjoined on one side by a transparent window (11), and with a reflector (30) disposed on the opposite side of the measuring chamber (16), which reflects the light striking it toward the outside through the measuring chamber (16) and the window (11), is particularly easy to clean and permits favorably reproducible measurements if another transparent window (33) is disposed between the reflector (30) and the measuring chamber (16) and this window (33) adjoins the measuring chamber (16) on the other side.

10 Claims, 2 Drawing Sheets

MEASURING CELL FOR LIQUIDS

The invention relates to a liquid measuring cell for measuring optical properties of liquids, in particular for NIR measurements, with a measuring chamber, which is adjoined on one side by a transparent window, and with a reflector disposed on the opposite side of the measuring chamber, which reflects the light striking it toward the outside through the measuring chamber and the window.

A liquid measuring cell of this type has been disclosed, for example, by DE 31 03 476 C2. The known liquid measuring cell is designated for the combined measurement of reflection and transmission properties (transflection) of liquids in the near infrared range NIR. To this end, it has a transparent measuring window on top through which the radiation of a radiation source enters a measuring chamber adjoining the measuring window, where it is partially reflected, partially scattered, and partially absorbed by the liquid. The portion of the radiation that passes through the liquid is diffusely reflected by a reflector, which has a rough gold surface and is disposed opposite the measuring window, and then passes through the liquid once more. The scattered and reflected portions then partially reemerge from the window. In the transmission, certain spectral ranges of the radiation are more intensely absorbed or scattered than others so that a spectral analysis of the diffuse light emerging from the measuring window permits conclusions to be drawn with regard to the type and quantity of constituents in the liquid tested.

In the known liquid measuring cell, the measuring chamber is adjoined on top by the measuring window and is adjoined on the bottom by the reflector. The surface of the reflector is therefore wet by the liquid. This device has the disadvantage that light-weight constituents of the liquid adhere to the rough surface of the reflector and change its optical properties. This severely impairs the reproducibility of the measurements, which has a particularly negative impact on series of measurements. This can in fact be remedied initially by frequently cleaning the reflector surface. But this is accompanied by a significant additional cost and does not produce satisfactory lasting results since frequent cleaning alters and finally destroys the optical properties of the rough surface. The reproducibility of the measurement results is in turn impaired as a result. Finally, when the surface coating is destroyed, the underlying material of the reflector as a rule suffers corrosion so that the entire reflector becomes unusable in the end.

The object of the current invention, therefore, is to disclose a liquid measuring cell of the type mentioned at the beginning, which is easy to clean and permits very reproducible measurements over long periods of time.

The object is attained according to the invention by virtue of the fact that another transparent window is disposed between the reflector and the measuring chamber and this additional window adjoins the measuring chamber on the other side.

With the device according to the invention, instead of coming into contact with the reflector surface, the liquid only comes in contact with the additional window. The window can be made of a smooth, easy-to-clean material, preferably glass, while the rough reflector surface is not wet and contaminated by the liquid. Therefore it does not need be cleaned and is thus also not subjected to wear. The additional window also sharply reduces the cost of cleaning and the possibly necessary replacement of the reflector and significantly improves the reproducibility of the measurement results. In this connection, this is surprising insofar as additional optical elements in the beam path fundamentally represent additional error sources which can also impair measurement results.

The uniformity of the layer thickness of the liquid, i.e. the thickness of the measuring chamber in the measuring region, is crucial to the reproducibility of the measurement results. In this connection, the device known from DE 31 03 476 C2 has the disadvantage that the O-ring seal disposed between the measuring window and reflector is elastic so that after the opening and closing of the measuring cell, the layer thickness is not reliably reproduced. Furthermore, slight deposits of the liquid form in particular on the surface of the O-ring, which must be expensively removed during cleaning.

Therefore, in order to improve the reproducibility of the measurement results and to make cleaning easier, a particularly simple embodiment of the invention is suggested in which the measuring chamber is embodied as a hollow space between a transparent bottom chamber part and a transparent top chamber part that rests on the bottom chamber part. There are no O-rings to become contaminated and the hard materials of the top chamber part and bottom chamber part that rest against each other continuously assure a precisely reproducible layer thickness in the measuring chamber. Since the measuring chamber is comprised of only two simply embodied components, it has practically no corners, edges, or recesses for impurities to become trapped in. It is thus particularly easy to clean.

A thorough cleaning is particularly simplified by means of the measure of embodying the top chamber part as removable because with the top chamber part removed, all of the inner surfaces that come into contact with the liquid are easily accessible for a mechanical cleaning.

In order to permit the manual removal of the top chamber part without special tools, it is suggested that the top chamber part be embodied in a cap-shaped fashion as a disk with an edge suitable for a screw or bayonet connection.

An embodiment that is simple and inexpensive to manufacture provides that the top chamber part is embodied as a plane-parallel disk, preferably a glass disk, whose underside rests against a flat surface of the bottom chamber part, and has a plane-parallel recess which, together with the surface of the bottom chamber part, defines the measuring chamber. The depth of the plane-parallel recess determines the layer thickness of the liquid to be tested and also essentially determines the volume of the measuring chamber.

In order to permit a simple and rapid change of the layer thickness, it is suggested that a number of interchangeable top chamber parts be provided, which have plane-parallel recesses with different depths.

The inflow and outflow of the liquids to be tested, during and after the measurements, requires liquid lines which lead into the measuring chamber at suitable locations. A simple embodiment of the liquid inlet and outlet provides that the bottom chamber part is provided with two conduits for the inflow and outflow of the liquid to be tested, which lead from the underside of the bottom chamber part to a liquid inlet and a liquid outlet of the measuring chamber. Then the continuing liquid lines can easily be connected to the conduits from the outside.

The reproducibility of the measurement results can be further improved by virtue of the fact that the bottom chamber part has an annular recess disposed in the edge region of the plane-parallel recess of the top chamber part and the conduits feed into this annular recess from radially opposing points. This measure assures that all the way around the measuring region, a slightly thicker bypass for the liquid is produced in which air bubbles possibly contained in the liquid, which could distort the measurement results, are conveyed around the measurement region.

In order to position the reflector as close to the measuring chamber as possible, the provision is made that the bottom chamber part has a central, cylindrical reflector bore which is let into it from its underside and which has the reflector disposed in it, where a preferably plane-parallel window region of the bottom chamber part between the reflector and the measuring chamber constitutes the additional transparent window. This window is relatively thin in comparison to the remaining thickness of the bottom chamber part due to the reflector bore that has been let into it so that an unfavorable optical absorption of the window is reduced and the heat transmission between the reflector and the measuring chamber is improved.

In a simple embodiment, the provision is made that the reflector is comprised of a reflector body with an essentially cylindrical top part whose end has a reflective layer affixed to it.

In order to keep the characteristics of the diffusely reflected radiation as true as possible, it is preferable that the reflective layer be comprised of a rough gold coating.

In a preferred embodiment, the reflector body is comprised of a favorably heat conductive material, preferably copper, and can be heated and/or cooled. This permits the temperature of the test liquid to be kept constant and thereby contributes to the improvement in the reproducibility of the measurement results which are very temperature dependent. Furthermore, the temperature can be kept constant with a very low expenditure of energy because the reflector body has a relatively low volume/mass ratio and is placed close to the measuring chamber. As a result, only a small amount of heat escapes unused into the environment or (during cooling operation) comes in from the environment. Since only smaller masses have to be heated/cooled, the adjusting time for a new temperature is very short.

In a modification of the invention, a Peltier element is provided as a heating and/or cooling element. The Peltier element only requires current and does not require an expensive water connection and a changeover from heating to cooling can be produced by simply reversing the current direction.

The measure that the reflector rests with its end against the window region of the bottom chamber part with an elastic initial stress, assures a good thermal contact with the measuring chamber and constant conditions in the optical transition between the window region of the bottom chamber part and the reflector, in particular, a plane-parallel contact without excessive pressure.

In order to prevent the distortion of measurement results due to mechanical stresses and flections of the optically active elements, it is suggested that a heat conducting intermediary piece connected to the heating element be provided to compensate for longitudinal expansion at different temperatures, and this intermediary piece has a preferably annular groove on top into which a preferably tubular bottom part of the reflector body is movably slid.

The heat transmission of this device can be still further improved by virtue of the fact that the groove is provided with a favorably heat conductive, permanently pasty material, preferably with heat conducting paste.

The initial stress required to press the reflector against the bottom chamber part can be produced simply in that a compensation disk or disk spring is disposed at the groove bottom in order to produce an elastic initial stress between the reflector body and the intermediary piece.

In order to improve the temperature constancy of the liquid sample, in the window region, the bottom chamber part has a temperature sensor which is preferably disposed eccentrically in the vicinity of the liquid inlet. This temperature sensor can cooperate with the heating/cooling element in a generally known control circuit in order to automatically stabilize the temperature of the liquid sample in relation to different environmental influences and in order to set a predetermined temperature from a designated range.

In order to largely eliminate interfering environmental influences and reduce the reaction time when adjusting and maintaining temperatures, it is suggested that in the window region, the bottom chamber part have a recess leading from the reflector bore, in which the temperature sensor is accommodated so that it is situated close to the surface of the bottom chamber part that adjoins the measuring window. The proximity to the liquid sample largely permits the temperature sensor to determine the true sample temperature without significant delay.

Other advantages and details of the invention ensue from the following description of an exemplary embodiment in conjunction with the drawings.

Figure 1:
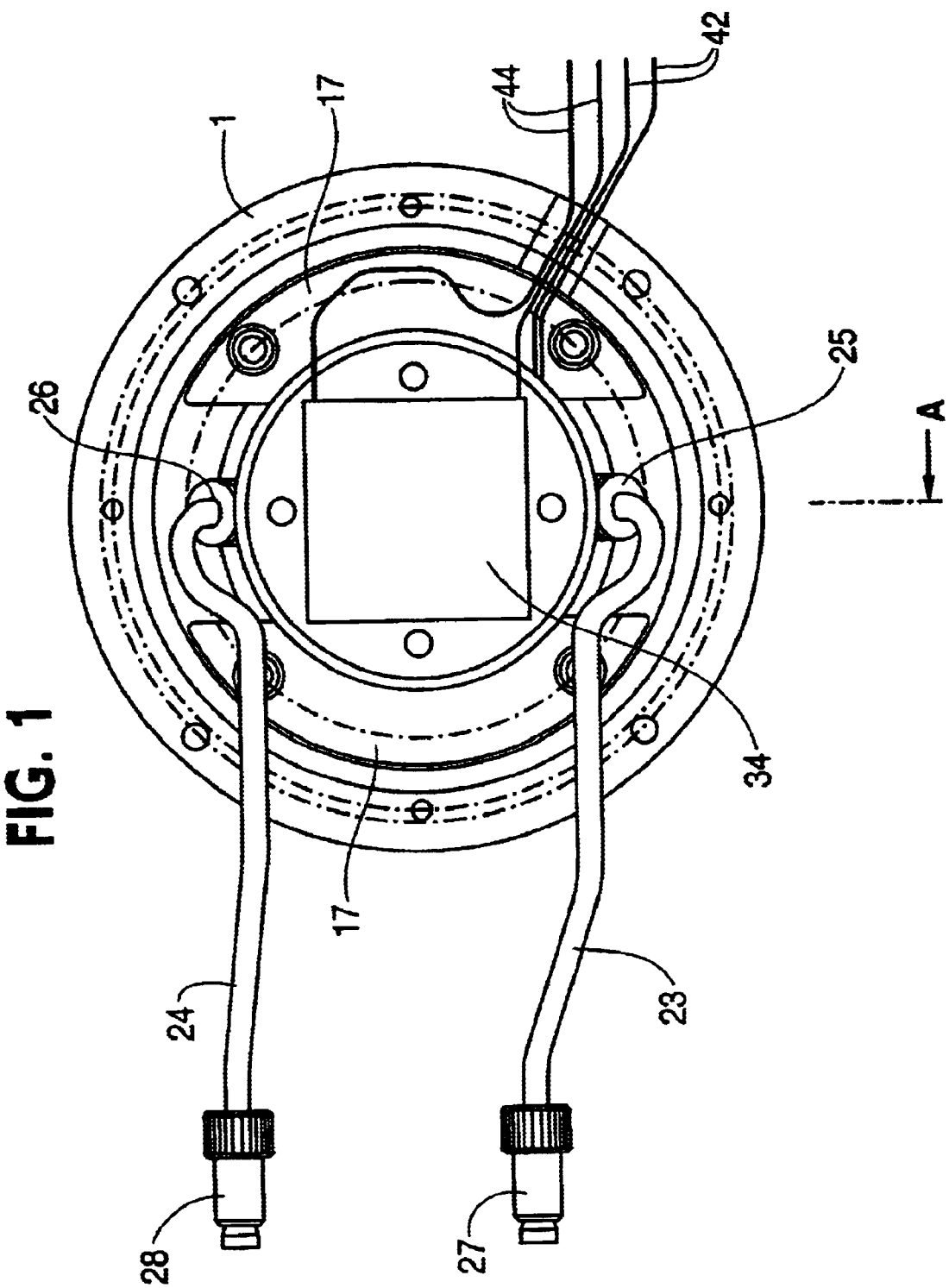
FIG. 1 shows a view from the underside of a liquid measuring cell according to the invention, with the bottom housing part removed.
Figure 2:
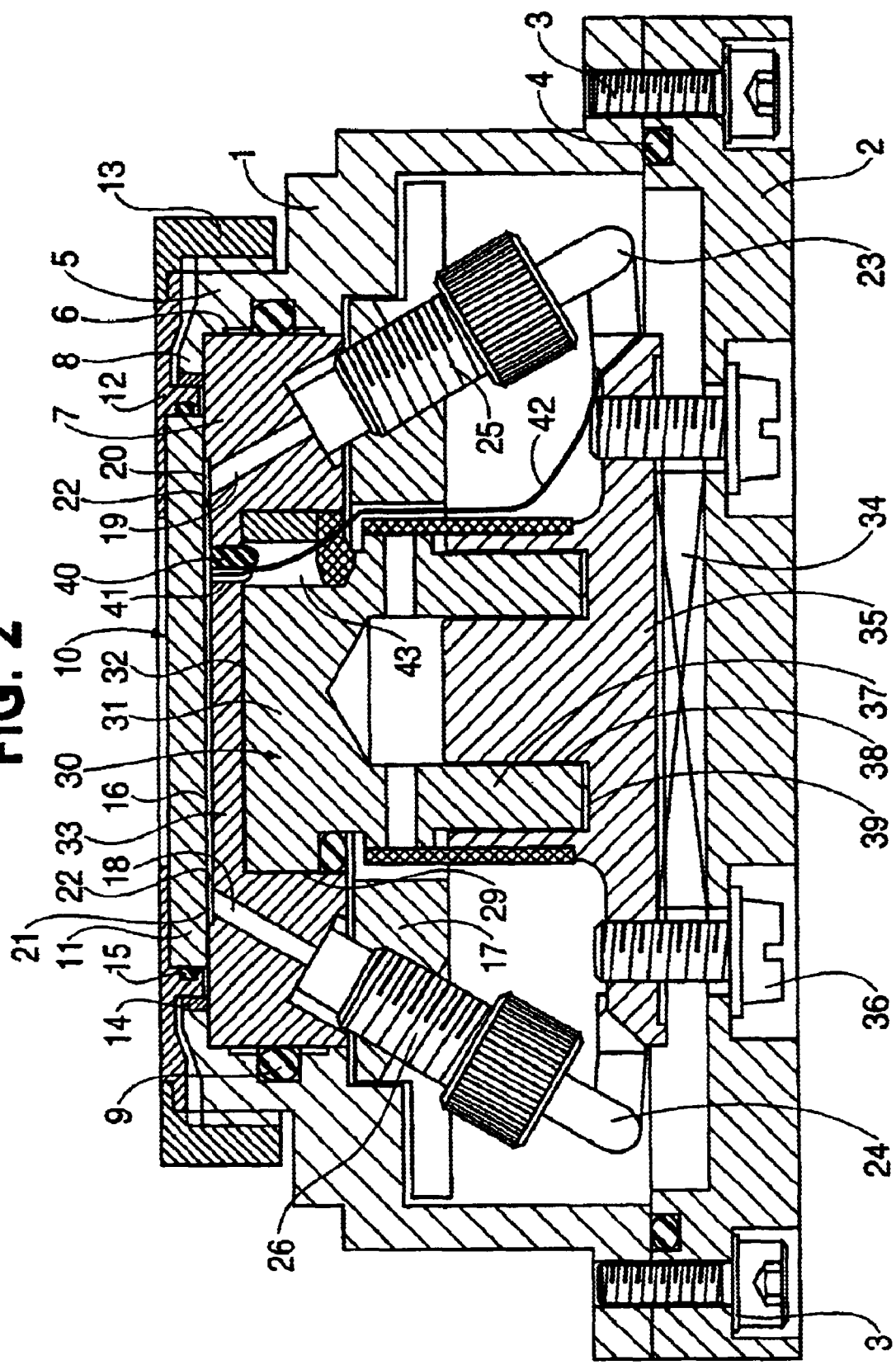
FIG. 2 is a section along line A in FIG. 1 through the same liquid measuring cell.

The liquid measuring cell according to the invention depicted in the Figures has a housing with an essentially collar-shaped top housing part 1 and a cap-like bottom housing part 2, which are connected to each other by means of housing screws 3 and are sealed by means of an O-ring seal 4.

In its upper region 5, the top housing part 1 has a large circular opening 6 which contains a bottom chamber part 7 made of glass. Toward the top, the bottom chamber part 7 rests against a radially inward protruding collar 8 of the top housing part 1 and is sealed in relation to it by means of another O-ring seal 9. From underneath, the bottom chamber part 7 is supported by a rest 17.

A cap-shaped top chamber part 10 is comprised of a transparent glass disk 11, which is inserted into an intermediary ring 12 and serves as a measuring window, and an edge 13, which is curved toward the top housing part 1 and is connected to the intermediary ring 12. The top chamber part 10 is placed on the top housing part 1, where the edge 13 encompasses the upper region 5 of the top housing part 1 and is detachably connected to it by means of a bayonet connection. The top chamber part 10 can be easily removed from the liquid measuring cell by detaching the bayonet connection.

An O-ring seal 14 between and inwardly pointing, annular projection of the intermediary ring 12 and the collar 8 of the top housing part 1 and an O-ring seal 15 between the above-mentioned annular projection and the circumference of the glass disk 11 are additionally provided in order to seal the liquid measuring cell. The O-ring 15 simultaneously constitutes a clamp retention, which secures the glass disk 11 to the intermediary ring 12 when the top chamber part 10 is removed.

By means of the above-described sealing concept, on the one hand, the liquid sample does not come into contact with the seals and on the other hand during assembly, only a constant force is required to close the cell because the O-rings are deformed by means of radial forces while the cell is closed with an axial force.

The measurement results are very dependent on the layer thickness of liquid through which the radiation passes. It is therefore crucial that this layer thickness remain constant over the entire measurement surface and over the measurement duration in order to assure comparable conditions with later measurements, in particular with interrelated series of measurements.

When the liquid measuring cell is closed, the top chamber part 10 rests on the bottom chamber part 7 and together with it, constitutes a hollow space, the measuring chamber 16, which contains the test liquid during the measurement. The thickness of the measuring chamber 16 is thus identical to the layer thickness of the liquid. In this instance, it is determined by the depth of a plane-parallel recess on the underside of the glass disk 11, which rests against the flat surface of the bottom chamber part 7 in the measuring region.

This device has the advantage that the various layer thicknesses/chamber thicknesses required for measuring different liquids can be simply produced through the use of a number of glass plates 11 with recesses of various depths. Instead of keeping a number of liquid measuring cells on hand, a simple changing the glass plate 11 is all that is required. In this case, the exchange can be simply carried out by detaching the bayonet connection, removing the top chamber part 10, and pushing the glass plate 11 out of its clamping retainer (O-ring 15). Than a different glass plate with a shallower or deeper recess is inserted into the intermediary ring 12. Then the top chamber part 10 is replaced and turned until the bayonet connection engages. Typically, experience has shown that five different glass plates in the layer thickness range from 50 $\mu$m to 800 $\mu$m are sufficient for all intended uses.

The bottom chamber part 7 has two conduits 18, 19 for the flow of the test liquid into and out of the measuring chamber 16. The conduits 18, 19 extend from the underside of the bottom chamber part 7 to a liquid inlet 20 and a liquid outlet 21 on top of the bottom chamber part 7.

The bottom chamber part 7 is provided with an annular recess 22, which is disposed radially in the edge region of the plane-parallel recess of the top chamber part 10 and encloses the measuring area. The liquid inlet 20 and the liquid outlet 21 feed into this annular recess 22 at radially opposite points. When the measuring chamber 16 is flushed with liquid, possibly present air bubbles preferably flow through the annular recess 22 and are thereby conveyed around the measuring area.

The liquid measuring cell is provided with an inlet line 23 and an outlet line 24 which are connected to the conduits 18, 19 of the bottom chamber part 7 by means of screw connections 25, 26. Other screw connections 27, 28 are disposed at the free ends of the lines 23, 24 situated outside the liquid measuring cell. They are used to connect the liquid measuring cell to a liquid reservoir from which liquid is supplied, for example by means of a pump, and to an outlet for the "used" liquid.

The bottom chamber part 7 is provided with a central reflector bore 29 let into it from the bottom, which is used to contain a reflector 30. The reflector 30 is comprised of a reflector body with a cylindrical top part 31 whose end 32 is provided with a rough gold coating as a reflective layer. The end 32 rests with initial stress against the top end surface of the reflector bore 29 where the glass bottom chamber part 7 has a plane-parallel transparent window region 33, which divides the reflective layer from the measuring chamber 16 and thus constitutes an additional window of the measuring chamber 16.

The reflector 30 is also used to temper the liquid in the measuring chamber 16 and is comprised of copper due to its favorable heat transmission properties. A Peltier element 34, which is fastened to the bottom housing part 2, is provided for heating and cooling. A heat conductive intermediary piece 35 is disposed between the Peltier element 34 and a reflector 30, and is fastened to the bottom housing part 10 by means of screws 36. In order to compensate for longitudinal expansion at different temperatures, the intermediary piece 35 and reflector 30 are embodied so that they can move axially in relation to each other. To this end, the reflector 30 has a tubular bottom part 37 which protrudes into an annular groove 38 on top of the intermediary piece 35. In order to improve the heat transmission, the groove 38 is filled with heat conducting paste. A compensation disk 39 is disposed at the bottom of the groove, serves as a spring, and elastically prestresses the reflector 30 in relation to the intermediary piece 35. This produces the elastic initial stress, which presses the reflector 30 against the window region 33 of the bottom chamber part 7, in order to assure a plane-parallel contact of the reflective layer.

In order to be able to determine and then also regulate the temperature of the test liquid inside the measuring chamber 16 as precisely as possible, the bottom chamber part 7 is provided with a temperature sensor 40 which is disposed eccentrically in the window region 33 in the vicinity of the liquid inlet 20 so that the regulation can react more rapidly to changing liquid temperatures. The temperature sensor 40 is accommodated in a recess 41 which extends up from the reflector bore 29 into close proximity of the surface of the bottom chamber part 7. As a result, the temperature sensor 40 is situated very close to the measuring chamber 16 and measures the true liquid temperature with a high degree of precision.

The electric supply lines 42 for the temperature sensor 40 are routed through a recess 43 of the reflector body 30 and finally out of the housing 1, 2, where they are connected to an electronic temperature regulating circuit that is not shown. The electric supply lines 44 for the Peltier element 34 also lead out of the housing 1, 2 to the temperature regulating circuit.

Due to its above-described special sealing concept, the liquid measuring cell according to the invention has a universal chemical resistance. It can easily be cleaned after the bayonet connection has been detached and the top chamber part 10 has been removed. The gold coating of the reflector 30 situated behind the glass of the window region 33 is always protected.

The liquid layer thickness can be rapidly changed by simply exchanging the glass disk 11 when the top chamber part 10 has been removed; the respectively desired layer thickness can be reproduced with a high degree of precision due to the precise manufacture of the glass parts 7, 10.

Because of the precise temperature measurement in the immediate vicinity of the liquid, a high degree of temperature constancy can be assured. Because of the favorable heat conduction to the measuring cell 16 (essentially copper) and the favorable thermal insulation of the measuring cell 16 in relation to the environment (essentially glass), on the one hand, new temperatures can be very rapidly set and on the other hand, there is only a relatively low heating or cooling demand which can be fulfilled by a small Peltier element 16. This in turn contributes to the compact design of the liquid measuring cell. Furthermore, the small Peltier element 16 can transmit the heat to the surrounding air by means of a suitable cooling body on the other side. This advantageously eliminates the need for an otherwise necessary water cooling and the attendant expense. Nevertheless, with the liquid measuring cell according to the invention, measuring temperatures of 10° C. to 60° C. can be adjusted in increments more precise than 0.3° C. at ambient temperatures of 5° C. to 40° C., which further improves reproducibility.

The liquid measuring cell according to the invention is suitable for testing liquid samples in the viscosity range from syrup to alcohol, and the specific contents and other features can be measured. The samples can be supplied manually by means of a syringe or automatically by means of a pump.

The samples in the measuring chamber 16 are tempered within an extremely short period of time so that comparable measuring conditions are produced very rapidly and the individual measurements are concluded within an extremely short period of time. A typical adjustment time is only two minutes. Particularly in extensive series measurements, this allows a very high number of individual measurements to be carried out within a given interval of time.

The actual spectroscopic measurements can be carried out, for example, as described in DE 31 03 476 C2, by means of an optical integration sphere with radiation detectors, where a suitable radiation source selects particular light wavelengths by means of a filter wheel as is described, for example, in U.S. Pat. No. 4,236,076.

Reference Numeral List 1 top housing part
2 bottom housing part
3 housing screw
4 O-ring seal
5 top region
6 opening
7 bottom chamber part
8 collar
9 O-ring seal
10 top chamber part
11 glass disk
12 intermediary ring
13 edge
14 O-ring seal
15 O-ring seal
16 measuring chamber
17 rest
18 conduit
19 conduit
20 liquid inlet
21 liquid outlet
22 annular recess
23 inlet line
24 outlet line
25 screw connection
26 screw connection
27 screw connection
28 screw connection
29 reflector bore
30 reflector
31 top part
32 end
33 window region
34 peltier element
35 intermediary piece
36 screw
37 bottom part
38 groove
39 compensation disk
40 temperature sensor
41 recess
42 supply line
43 recess
44 supply line

What is claimed is:

1. A liquid measuring cell for measuring optical properties of liquids, comprising:

a measuring chamber, said measuring chamber adjoined on one side by a transparent window;

a reflector disposed on the opposite side of the measuring chamber, wherein said reflector reflects the light striking it toward the outside through the measuring chamber and the window; and another transparent window, said second transparent window being disposed between the reflector and the measuring chamber and adjoining the measuring chamber on the other side, wherein the measuring chamber comprises a hollow space between a transparent bottom chamber part and a transparent top chamber part that rests on the bottom chamber part, and the top chamber part is embodied in a cap-shaped fashion as a disk with a suitable edge that is embodied as a screw or bayonet connection, and the top chamber part comprises a plane-parallel disk whose underside rests against a flat surface of the bottom chamber part; and a plane-parallel recess which, together with the surface of the bottom chamber part, defines the measuring chamber.

2. The liquid measuring cell according to claim 1, wherein a number of interchangeable top chamber parts are provided, which have plane-parallel recesses with different depths.

3. The liquid measuring cell according to claim 1 wherein the bottom chamber part further comprises a central, cylindrical reflector bore which is let into it from its underside and which has the reflector disposed in it; and a plane-parallel window region of the bottom chamber part between the reflector and the measuring chamber constituting the additional transparent window, wherein the reflector is comprised of a reflector body with an essentially cylindrical top part whose end has a reflective layer affixed to it, and the reflective layer is comprised of a rough gold coating.

4. The liquid measuring cell according to claim 3, wherein the reflector body is comprised of a favorably heat conductive material, and can be heated and/or cooled by means of a heating/cooling element.

5. The liquid measuring cell according to claim 4, wherein a Peltier element is provided as the heating/cooling element.

6. A liquid measuring cell for measuring optical properties of liquids, comprising:

a measuring chamber, said measuring chamber adjoined on one side by a transparent window;

a reflector disposed on the opposite side of the measuring chamber, wherein said reflector reflects the light striking it toward the outside through the measuring chamber and the window;

another transparent window, said second transparent window being disposed between the reflector and the measuring chamber and adjoining the measuring chamber on the other side;

wherein the measuring chamber comprises a hollow space between a transparent bottom chamber part and a transparent top chamber part that rests on the bottom chamber part;

the bottom chamber part further comprising
- a central, cylindrical reflector bore which is let into it from its underside and which has the reflector disposed in it;
- a plane-parallel window region of the bottom chamber part between the reflector and the measuring chamber constituting the additional transparent window;

wherein the reflector is comprised of a reflector body with an essentially cylindrical top part whose end has a reflective layer affixed to it;

the reflector body is comprised of a favorably heat conductive material, and can be heated and/or cooled by means of a heating/cooling element; and the heating/cooling element comprising a heat conducting intermediary piece connected to the heating element to compensate for longitudinal expansion at different temperatures, said intermediary piece having an annular groove on top into which a tubular bottom part of the reflector body is movably slid.

7. The liquid measuring cell according to claim 6, the groove further comprising a heat conducting paste.

8. The liquid measuring cell according to claim 6, further comprising a compensation disk or disk spring disposed at the bottom of the groove in order to produce an elastic stress between the reflector body and the intermediary piece.

9. The liquid measuring cell according to claim 1, wherein, in the window region, the bottom chamber part has a temperature sensor which is disposed eccentrically in the vicinity of a liquid inlet.

10. The liquid measuring cell according to claim 9, wherein, in the window region, the bottom chamber part further comprises a recess extending from the reflector bore, the temperature sensor being accommodated in this recess so that it is situated close to a surface of the bottom chamber part adjoining the measuring chamber.

* * * * *